(12) United States Patent
Stensen et al.

(10) Patent No.: US 9,556,223 B2
(45) Date of Patent: *Jan. 31, 2017

(54) ANTIMICROBIAL COMPOUNDS

(75) Inventors: Wenche Stensen, Kvaloysletta (NO); Frederick Alan Leeson, Tromso (NO); Øystein Rekdal, Tromso (NO); John Sigurd Svendsen, Kvaloysletta (NO)

(73) Assignee: LYTIX BIOPHARMA AS, Tromso (NO)

( * ) Notice: Subject to any disclaimer, the term of this patent is extended or adjusted under 35 U.S.C. 154(b) by 578 days.

This patent is subject to a terminal disclaimer.

(21) Appl. No.: 13/122,156

(22) PCT Filed: Oct. 2, 2009

(86) PCT No.: PCT/GB2009/002365
§ 371 (c)(1),
(2), (4) Date: Aug. 19, 2011

(87) PCT Pub. No.: WO2010/038041
PCT Pub. Date: Apr. 8, 2010

(65) Prior Publication Data
US 2011/0301076 A1   Dec. 8, 2011

(30) Foreign Application Priority Data
Oct. 2, 2008 (GB) .................................. 0818072.1

(51) Int. Cl.
C07K 5/09 (2006.01)
C07K 17/00 (2006.01)
A61K 38/00 (2006.01)

(52) U.S. Cl.
CPC ............. *C07K 5/0817* (2013.01); *A61K 38/00* (2013.01); *C07K 17/00* (2013.01)

(58) Field of Classification Search
None
See application file for complete search history.

(56) References Cited

U.S. PATENT DOCUMENTS 8,598,114 B2 * 12/2013 Stensen et al. ................ 514/3.3
2002/0035239 A1   3/2002 Andersen et al.
(Continued)

FOREIGN PATENT DOCUMENTS

WO      03097664 A2    11/2003
WO   2004/110341 A2    12/2004
WO   2006086321 A2     8/2006

OTHER PUBLICATIONS

Svenson Johan et al., "Albumin binding of short cationic antimicrobial micropeptides and its influence on the in vitro bactericidal effect", Journal of Medicinal Chemistry, American Chemical Society, Washington, US vol. 50, No. 14, Jul. 12, 2007, pp. 3334-3339 (also cited in IDS of Jun. 18, 2012).*

(Continued)

*Primary Examiner* — Maury Audet
(74) *Attorney, Agent, or Firm* — Fox Rothschild LLP

(57) ABSTRACT

The present invention relates to a compound of formula (I) AA-AA-AA-$R_1$—$R_2$ (I) wherein, in any order, 2 of said AA (amino acid) moieties are cationic amino acids and 1 of said AA is an amino acid with a lipophilic R group, the R group having 14-27 non-hydrogen atoms; $R_1$ is a N atom, which may be substituted by a branched or unbranched $C_1$-$C_{10}$ alkyl or aryl group, which group may incorporate up to 2 heteroatoms selected from N, O and S; and $R_2$ is an aliphatic moiety having 2-20 non-hydrogen atoms, said moiety being linear, branched or cyclic. The invention further relates to formulations containing these compounds, solid supports having these compounds attached thereto, the use of these compounds in therapy, particularly as antimicrobial, antitumor or anti-biofilm agents and non-therapeutic uses of these compounds, particularly their use in inhibiting biofilm formation or removing a biofilm.

11 Claims, 7 Drawing Sheets

(56) References Cited

U.S. PATENT DOCUMENTS

Figure 1:
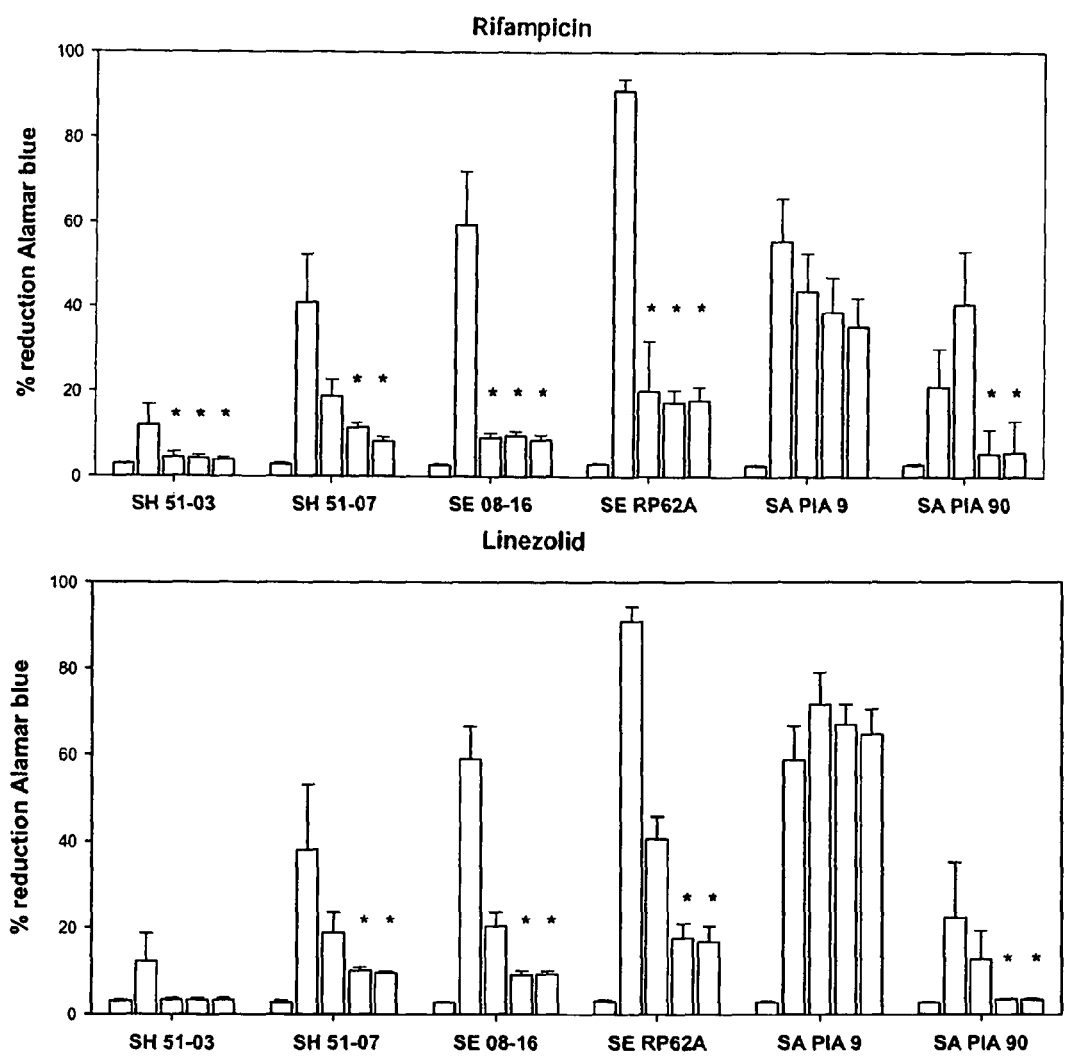
Figure 1:
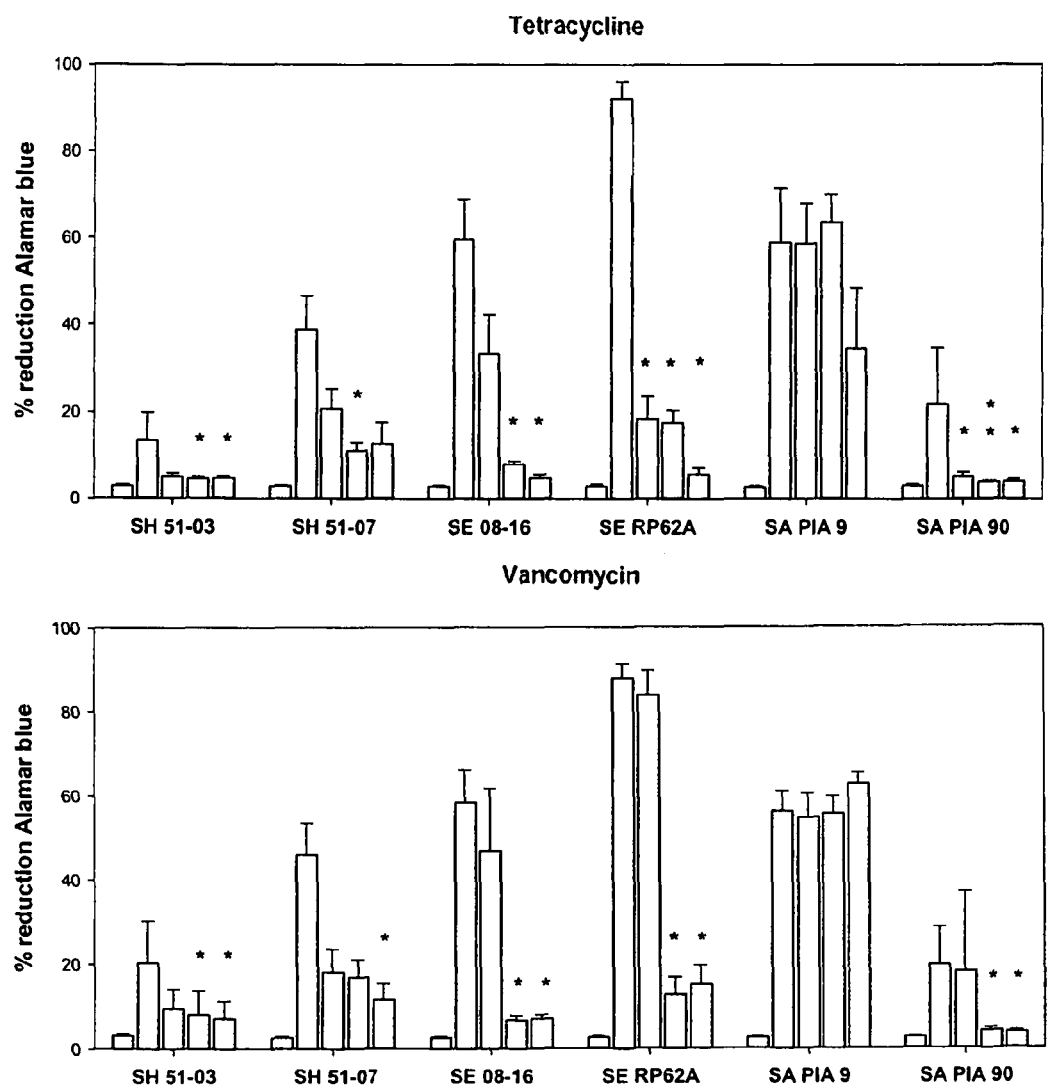

| | | | |
|---|---|---|---|
| 2003/0050247 A1* | 3/2003 | Kuhner et al. | 514/16 |
| 2007/0072808 A1 | 3/2007 | Shai et al. | |
| 2011/0143384 A1* | 6/2011 | Stensen et al. | 435/23 |
| 2011/0172145 A1* | 7/2011 | Stensen et al. | 514/3.3 |
| 2011/0301076 A1* | 12/2011 | Stensen et al. | 514/2.3 |

OTHER PUBLICATIONS

Svenson Johan et al., "Antimicrobial peptides with stability toward tryptic degradation", Biochemistry, American Chemical Society, Easton, PA, US, vol. 47, No. 12, Mar. 25, 2008, pp. 3777-3788 (also cited in IDS of Jun. 18, 2012).*

Haug Bengt Erik et al., "Bulky nonproteinogenic amino acids permit the design of very small and effective cationic antibacterial peptides", Journal of Medicinal Chemistry, American Chemical Society, Washington, US, vol. 47, No. 17, Aug. 12, 2004, pp. 4159-4162 (also cited in IDS of Jun. 18, 2012).*

Haug et al. Synthetic antimicrobial peptidomimetics with therapeutic potential. J Med Chem. Jul. 24, 2008;51(14):4306-14. doi: 10.1021/jm701600a. Epub Jun. 21, 2008.*

Svenson, Johan; Brandsdal, Bjorn-Olav; Stensen, Wenche; Svendsen, John S. Albumin Binding of Short Cationic Antimicrobial Micropeptides and Its Influence on the in Vitro Bactericidal Effect. Journal of Medicinal Chemistry (2007), 50(14),3334-3339.*

Cirioni et al. (The lipopeptides Pal-Lys-Lys-NH(2) and Pal-Lys-Lys soaking alone and in combination with intraperitoneal vancomycin prevent vascular graft biofilm in a subcutaneous rat pouch model of staphylococcal infection. Peptides. Jun. 2007;28(6):1299-303. Epub Mar. 31, 2007.*

Svenson Johan et al., "Albumin binding of short cationic antimicrobial micropeptides and its influence on the in vitro bactericidal effect", Journal of Medicinal Chemistry, American Chemical Society, Washington, US vol. 50, No. 14, Jul. 12, 2007, pp. 3334-3339.

Svenson Johan et al., "Antimicrobial peptides with stability toward tryptic degradation", Biochemistry, American Chemical Society, Easton, PA, US, vol. 47, No. 12, Mar. 25, 2008, pp. 3777-3788.

Haug Bengt Erik et al., "Bulky nonproteinogenic amino acids permit the design of very small and effective cationic antibacterial peptides", Journal of Medicinal Chemistry, American Chemical Society, Washington, US, vol. 47, No. 17, Aug. 12, 2004, pp. 4159-4162.

Cirioni et al., "The lipopeptides Pal-Lys-Lys-NH2 and Pal-Lys-Lys soaking alone and in combination with intraperitoneal vancomycin prevent vascular graft biofilm in a subcutaneous rat pouch model of staphylococcal infection", Peptides, Elsevier, Amsterdam, vol. 28, No. 6, Jun. 1, 2007, pp. 1299-1303.

Wei et al., "Effect of MUC7 peptides on the growth of bacteria and on *Streptococcus mutans* biofilm", JAC, vol. 57, Apr. 4, 2006, pp. 1100-1109.

Beckloff et al., "Activity of an Antimicrobial Peptide Mimetic against Planktonic and Biofilm Cultures of Oral Pathogens", Antimicrob. Agents Chemother, vol. 51, Sep. 4, 2007, pp. 4125-4132.

Haug et al., "Synthetic antimicrobial peptidomimetics with therapeutic potential", J. Med. Chem, vol. 51, 2008, pp. 4306-4314.

Haug et al., "The medicinal chemistry of short lactoferricin-based antibacterial peptides", Curr. Med. Chem, vol. 14, 2007, pp. 1-18.

Altman et al., "In vitro assessment of antimicrobial peptides as potential agents against several oral bacteria", JAC, vol. 58, May 10, 2006, pp. 198-201.

Eckert et al., "Targeted killing of *Streptococcus mutans* by a pheromone-guided "smart" Antimicrobial Peptide", Antimicrobial Agents Chemother, vol. 50, Oct. 23, 2006, pp. 3651-3657.

Lasa, "Towards the identification of the common features of bacterial biofilm development", International Microbiol, vol. 9, 2006, pp. 21-28.

Donlan et al., "Biofilms: Survival Mechanisms of Clinically Relevant Microorganisms", Clinical Microbiol, vol. 15, 2002, pp. 167-193.

Haug, et al. Novel Antibacterial Tripeptides. Peptide Science 71(3): 310. (2003).

Haug, et al. "Bulky Nonproteinogenic Amino Acids Permit the Design of Very Small and Effective Cationic Antibacterial Peptides." J Med Chem 47(17): 4159-4162. (2004).

Strom, et al. "The Pharmacophore of Short Cationic Antibacterial Peptides." J Med Chem 46(9): 1567-1570. (2003).

* cited by examiner

ANTIMICROBIAL COMPOUNDS

The present application is the U.S. National Phase of International Patent Application Serial No. PCT/GB2009/002365, filed Oct. 2, 2009, which claims the benefit of United Kingdom Patent Application Serial No. 0818072.1, filed Oct. 2, 2008, the disclosures of which are hereby incorporated by reference in their entireties.

The present invention relates to peptides and similar molecules which exhibit antimicrobial activity, in particular which exhibit that activity against microorganisms existing as a biofilm.

Peptides and their derivatives have long been recognised as therapeutically interesting molecules. A wide variety of organisms use peptides as part of their host defence mechanism. Antimicrobial peptides have been isolated from species as diverse as bacteria and mammals. Generally, these peptides have a net positive charge and a propensity to form amphiphilic α-helix or β-sheet structures upon interaction with the outer phospholipid bilayer in bacterial cell membranes. In most cases the detailed molecular mechanisms of the antibiotic action are unknown, although some peptides categorised as class L (lytic) peptides are believed to interact with bacterial cell membranes, probably forming ion-channels or pores.

The majority of known antibacterial peptides comprise 10 or more, typically 20 or more amino acids, this number of amino acid being required in order to provide sufficient length for the peptide, generally in α-helical form, to span the bacterial cell membrane and form a pore. Such a mechanism is the generally accepted way in which the majority of such peptides exert their cytotoxic activity.

Synthesis of the antibacterial peptides of the prior art can be difficult, and typically requires the peptides to be synthesised by bacteria or other organisms which can be cultured and harvested to yield the peptide of interest, additional processing steps after isolation of the direct product of translation are generally required. If active peptides could be identified which were shorter, this would enable economic manufacture by synthesis from the amino acid building blocks or available di- or tri-peptides. In addition, short peptides would offer advantages for biodelivery. There is a growing demand for antibiotics which can be administered without the need for an injection, such as by inhalation and absorption across the blood capillaries of the nasal passages.

The search for novel antibiotics has taken on particular urgency because of the increasing number of bacterial strains which are exhibiting resistance to known and extensively used drugs. Those operating in the fields of medicine as well as agriculture, environmental protection and food safety are constantly requiring new antibacterial agents and may have to treat a given population or site with several different antibacterial agents in order to effectively combat the undesirable bacteria.

A biofilm is a collection, or community, of microorganisms surrounded by a matrix of extracellular polymers (also known in the art as a glycocalyx). These extracellular polymers are typically polysaccharides, notably polysaccharides produced by the organisms themselves, but they can contain other biopolymers as well. A biofilm will typically be attached to a surface, which may be inert or living, but it has also been observed that biofilms may form from microorganisms attached to each other or at any interface. Such a mode of growth is protective to the microorganisms, and renders them difficult to remove or eradicate. Biofilms cause significant commercial, industrial and medical problems, in terms of infections, contamination, fouling and spoilage etc.

Formation of a biofilm typically begins with the attachment of free-floating microorganisms to a surface. These first colonists may adhere to the surface initially through weak, reversible van der Waals forces. If the colonists are not immediately separated from the surface, they can anchor themselves more permanently using cell adhesion structures such as pili.

The first colonists typically facilitate the arrival of other cells by providing more diverse adhesion sites and beginning to build the matrix that holds the biofilm together. Some species are not able to attach to a surface on their own but are often able to anchor themselves to the matrix or directly to earlier colonists. During this colonization the cells are able to communicate via quorum sensing. Once colonization has begun, the biofilm may grow through a combination of cell division and recruitment. The final stage of biofilm formation is known as development, and is the stage in which the biofilm is established and may only change in shape and size. This development of biofilm allows for the cells to become more antibiotic resistant. A biofilm in the "development" stage may be referred to as a "mature" biofilm.

The microorganisms in a biofilm community display properties at the cellular level (phenotype) that are not shared by their planktonic (free-floating) equivalents. It is believed that such sessile microorganisms are profoundly different from planktonic free-floating cells. Further differences can be also be observed at the community level and are attributed to the effects of the extracellular matrix. Perhaps most notable is the commonly observed phenomenon that microorganisms in a biofilm environment do not display the same susceptibilities to anti-microbial agents, e.g. antibiotics, antifungals and microbicides, and host immune defences or clearance mechanisms. It is thought that this resistance is due to the barrier effect of the extracellular matrix and/or a phenotypic change in the microbes themselves. It is also believed that microorganisms in biofilms may grow more slowly, and as a result take up anti-microbial agents more slowly.

There exists a need therefore for new antimicrobial agents which are effective antibiofilm agents, particularly in clinical contexts.

The present inventors have now identified a small group of modified peptides which exhibit an impressive set of characteristics, including good antimicrobial activity and low toxicity and specifically a good activity against microorganisms which are present in biofilms.

Thus in one aspect is provided a compound, preferably a peptide, of formula (I)

$$AA\text{-}AA\text{-}AA\text{-}R_1\text{—}R_2 \qquad (I)$$

wherein, in any order, 2 of said AA (amino acid) moieties are cationic amino acids, preferably lysine or arginine but may be histidine or any non-genetically coded or modified amino acid carrying a positive charge at pH 7.0, and 1 of said AA is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms (in the case of fused rings of course the non-hydrogen atoms may be shared);

$R_1$ is a N atom, which may be but preferably is not substituted by a branched or unbranched $C_1\text{-}C_{10}$ alkyl or aryl group, e.g. methyl, ethyl or phenyl, and this group may incorporate up to 2 heteroatoms selected from N, O and S;

$R_2$ is an aliphatic moiety having 2-20 non-hydrogen atoms, preferably these are carbon atoms but oxygen, nitrogen or sulphur atoms may be incorporated, preferably $R_2$ comprises 3-10, most preferably 3-6 non-hydrogen atoms and the moiety may be linear, branched or cyclic. If the $R_2$ group comprises a cyclic group this is preferably attached directly to the nitrogen atom of $R_1$.

Preferred compounds of the invention incorporate an $R_2$ group which is linear or branched, in particular a linear or branched alkyl group including ethyl, propyl, isopropyl, butyl, isobutyl, sec-butyl, tert-butyl, pentyl and isomers thereof, hexyl and isomers thereof etc.; propyl, isopropyl, butyl and isobutyl are especially preferred.

Of the $R_2$ groups which comprise a cyclic group, preferred are molecules in which $R_2$ is cyclohexyl or cyclopentyl.

Suitable non-genetically coded amino acids and modified amino acids which can provide a cationic amino acid include analogues of lysine, arginine and histidine such as homolysine, ornithine, diaminobutyric acid, diaminopimelic acid, diaminopropionic acid and homoarginine as well as trimethyllysine and trimethylornithine, 4-aminopiperidine-4-carboxylic acid, 4-amino-1-carbamimidoylpiperidine-4-carboxylic acid and 4-guanidinophenylalanine.

The large lipophilic R group may contain hetero atoms such as O, N or S but typically there is no more than one heteroatom, preferably it is nitrogen. This R group will preferably have no more than 2 polar groups, more preferably none or one, most preferably none.

In a preferred embodiment the compounds, preferably peptides, of the invention are of formula (II)

$$AA_1\text{-}AA_2\text{-}AA_1\text{-}R_1\text{—}R_2 \quad (II)$$

wherein:

$AA_1$ is a cationic amino acid, preferably lysine or arginine but may be histidine or any non-genetically coded or modified amino acid carrying a positive charge at pH 7.0;

$AA_2$ is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms; and $R_1$ and $R_2$ are as defined above.

Further compounds of the invention include compounds of formulae (III) and (IV):

$$AA_2\text{-}AA_1\text{-}AA_1\text{-}R_1\text{—}R_2 \quad (III)$$

$$AA_1\text{-}AA_1\text{-}AA_2\text{-}R_1\text{—}R_2 \quad (IV)$$

wherein $AA_1$, $AA_2$, $R_1$ and $R_2$ are as defined above. However molecules of formula (II) are preferred.

As discussed further below, compounds of the invention may be peptide mimetics, in particular with linkages other than amide bonds between said AA moieties, nevertheless, amide linkages are preferred.

From amongst the above compounds certain are preferred. In particular, compounds wherein the amino acid with a large lipophilic R group, conveniently referred to herein as $AA_2$, is tributyl tryptophan (Tbt) or a biphenylalanine derivative such as Phe (4-(2'-naphthyl)), Phe (4-(1'-naphthyl)), Phe (4-4'-n-butylphenyl), Phe (4-4'-biphenyl) or Phe (4-4'-t-butylphenyl); Phe (4-(2'-naphthyl)) and Tbt being most preferred.

A further preferred group of compounds are those in which —$R_1$—$R_2$ together is selected from the group consisting of —NHCH($CH_3$)$_2$, —NH($CH_2$)$_5$$CH_3$, —NH($CH_2$)$_3$$CH_3$, —NH($CH_2$)$_2$$CH_3$, —NHCH$_2$CH($CH_3$)$_2$, —NHcyclohexyl and —NHcyclopentyl, most preferred are compounds in which —$R_1$—$R_2$ is the group —NHCH($CH_3$)$_2$ or —NH($CH_2$)$_5$$CH_3$.

The compounds include all enantiomeric forms, both D and L amino acids and enantiomers resulting from chiral centers within the amino acid R groups and $R_2$.

From hereon when referring to amino acids, standard single-letter amino acid abbreviations or standard three-letter amino acid codes may be used.

Preferred compounds are those of table 1 herein and their equivalents in which Arg residues have been replaced with alternative cationic residues, e.g., Lys.

Most preferred compounds are Compounds 1 and 2 in the Examples herein and their equivalents incorporating other cationic residues in place of Arg.

In a further aspect is provided compounds of formulae (I), (II), (III) or (IV) for use in therapy, particularly for use as an antimicrobial (e.g. antibacterial) agent, but also as an antitumour agent. The compounds of the invention are also for use in treating biofilm-associated infections.

Such antimicrobial molecules also have non-therapeutic uses, for example in agriculture or in domestic or industrial situations as sterilising agents for materials susceptible to microbial contamination. Thus, in a further aspect, the present invention provides the use of the compounds of the invention as antimicrobial, particularly as antibacterial agents. Biofilms are known to cause problems in environmental settings and the present invention further provides a method of inhibiting biofilm formation or removing a biofilm which comprises contacting said biofilm with a compound of the invention.

A 'biofilm-associated infection' is a microbial infection of a subject where it is known or suspected that the microbes are present as a biofilm. Typically it will be an infection where the existence of a biofilm is relevant to the clinical condition, e.g. to the diagnosis or prognosis, to the treatment regimen, to the severity of the infection, to the duration of the infection up to the point of treatment or anticipated in the future. 'Treatment' includes prophylactic treatment and encompasses a reduction in size of the biofilm, a reduction in number of living microorganisms within the biofilm and prevention or reduction in the tendency of microorganisms within the biofilm to break free and form new biofilm colonies. Treatment includes an improvement, observed by clinician or patient, in one or more of the symptoms associated with the infection.

The size, structure, integrity, and number of microbes in a biofilm can be analysed by any convenient method. For instance, scanning and transmission electronic microscopy is often used to assess the size, integrity and structure of a biofilm. Analysis of biofilm is described in the Examples hereto.

The biofilms that may be treated in accordance with the invention are not limited in terms of the microorganisms they contain, the lytic molecules described herein target the cell membranes and therefore have a fairly non-specific activity. Accordingly, the biofilm may comprise any class, genus or species of microorganism, namely any microorganism that may form a biofilm. Such microorganisms typically include bacteria, including any genus or species of bacteria. Thus, the bacteria may be gram positive or gram negative, or gram test non-responsive. They may be aerobic or anaerobic. The bacteria may be pathogenic or non-pathogenic.

It is particularly surprising that the molecules defined herein are able to kill bacteria in mature biofilms and the treatment of such biofilms is particularly preferred.

The biofilm may comprise Gram positive bacteria, *Pseudomonas aeruginosa* and/or fungi. Biofilms comprising or consisting of Gram positive bacteria are preferred targets.

Biofilms comprising *Staphylococcus* are preferred targets, with biofilms comprising *S. haemolyticus* being especially preferred.

Biofilms may also contain fungi, algae and other organisms such as parasitic protozoa. Mixed colony biofilms are known and treatable according to the methods described herein.

Chronic wounds are discussed above and are a preferred therapeutic target, these include diabetic foot ulcers, venous leg ulcers and pressure ulcers as well as surgical wounds (postoperative wound infections) which have become chronic.

Medical devices are a particular class of surface on which a biofilm may form and represent a further preferred therapeutic target according to the present invention.

This may include any kind of line, including catheters (e.g. central venous and urinary catheters), prosthetic devices e.g., heart valves, artificial joints, false teeth, dental crowns, dental caps and soft tissue implants). Any kind of implantable (or "in-dwelling") medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

In specific embodiments of the invention the peptides and peptidomimetics may be used in the treatment of native valve endocarditis, acute otitis media, chronic bacterial prostatitis, pneumonia, dental plaque, periodontitis, biofilm infections in respiratory diseases, which may include cystic fibrosis, and device related infection associated with implantable or prosthetic medical devices e.g. prosthetic valve endocarditis or infection of lines or catheters or artificial joints or tissue replacements.

The wounds may be acute or chronic. Acute wounds are wounds that proceed orderly through the three recognised stages of the healing process (i.e. the inflammatory stage, the proliferative stage and the remodelling phase) without a protracted time course. Chronic wounds, however, are those wounds that do not complete the ordered sequence of biochemical events because the wound has stalled in one of the healing stages. Viewed alternatively a chronic wound is a wound that has not healed within at least 40 days, preferably at least 50 days, more preferably at least 60 days, most preferably at least 70 days.

The wound to be treated may be a breach in, or denudement of, the tissue for instance caused by surgical incision or trauma, e.g., mechanical, thermal, electrical, chemical or radiation trauma; a spontaneously forming lesion such as a skin ulcer (e.g. a venous, diabetic or pressure ulcer); a blister (e.g. a friction or thermal blister or a blister caused by pathogen infection such as chicken pox); an anal fissure or a mouth ulcer.

The treatment of chronic wounds represents a particularly preferred aspect of the present invention.

Although biofilms are now more widely recognised as contributing to medical conditions, they are also implicated in non-medical problems caused by microbial colonisation of surfaces. This may be, for example, in domestic, industrial, research or hospital settings where surfaces need to be kept free of bacterial contamination.

As noted above the biofilm may be present on a surface. The surface is not limited and includes any surface on which a microorganism may occur, particularly, as noted above, a surface exposed to water or moisture. The surface may be biotic or abiotic, and inanimate (or abiotic) surfaces include any such surface which may be exposed to microbial contact or contamination. Thus particularly included are surfaces on machinery, notably industrial machinery, or any surface exposed to an aquatic environment (e.g. marine equipment, or ships or boats or their parts or components), or any surface exposed to any part of the environment e.g. pipes or on buildings. Such inanimate surfaces exposed to microbial contact or contamination include in particular any part of: food or drink processing, preparation, storage or dispensing machinery or equipment, air conditioning apparatus, industrial machinery e.g. in chemical or biotechnological processing plants, storage tanks and medical or surgical equipment. Any apparatus or equipment for carrying or transporting or delivering materials, which may be exposed to water or moisture is susceptible to biofilm formation. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

Thus in a further aspect the present invention provides a method of inhibiting biofilm formation or removing a biofilm which comprises contacting said biofilm with a peptide or peptidomimetic as defined herein. Said biofilm may be on any of the surfaces described above.

The term "contacting" encompasses any means of delivering the peptide or peptidomimetic to the biofilm, whether directly or indirectly, and thus any means of applying the peptide or mimetic to the biofilm or exposing the biofilm to the peptide or mimetic e.g. applying the peptide or mimetic directly to the biofilm.

Optionally, the compounds of the present invention may be attached to a solid support, for example in order to prevent the colonization of bacteria thereon. Thus, in addition to their use in the sterilisation of contaminated surfaces, the present compounds can be attached to surfaces in order to prevent their contamination. In particular, the present compounds can be attached to solid supports in order to inhibit the formation of a biofilm thereon. In the context of the present invention, the terms "solid support" and "surface" are interchangeable.

Thus, in a further aspect is provided a solid support is provided having attached thereto a compound of the present invention. Such solid supports include but are not limited to the surfaces described above. Surfaces on which biofilms can form include medical devices, containers, carriers or ducts carrying water or other fluids etc. Medical devices are a particular class of surface on which a biofilm may form and represent a preferred surface onto which the compounds of the present invention can be attached.

The term "medical devices" includes any kind of line, including catheters (e.g. central venous and urinary catheters), prosthetic devices e.g., heart valves, artificial joints, false teeth, dental crowns, dental caps and soft tissue implants). Any kind of implantable (or "in-dwelling") medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

The compounds of the present invention can be attached to solid supports by any means known in the art. The compounds may be directly or indirectly attached to the solid support, i.e. they may be attached by a linking group. Preferably the molecules are directly attached to the solid support although, as discussed below, modification of the compounds of the invention may be required to permit attachment. Typically, the compounds are covalently attached to a desired solid support. Therefore, optionally the compounds of the present invention comprise a chemical group which permits covalent attachment to said solid support. Alternatively, the compounds are modified to permit covalent attachment to said solid support.

The term "modified" or "modification" includes the replacement of a chemical group of a compound of the invention with a chemical group which, permits covalent attachment to said support. The term also includes the further substitution of an existing chemical group with a chemical group which permits covalent attachment to said support. The term also includes the scenario where, rather than replacing or further substituting a chemical group of a pre-existing compound of the present invention, a compound of the invention is designed to comprise a chemical group which permits covalent attachment to said solid support, and is prepared in this form. Preferably said modification results in the introduction of no more than 5, preferably no more than 3, more preferably no more than 2 non-hydrogen atoms.

The exact nature of the chemical group will depend on the chemical nature of the desired surface to which the compound is to be attached. Likewise, the surface of the solid support may be modified to enable attachment. A variety of suitable chemical groups are well-known in the art and the appropriate groups for attachment would be readily determinable by the skilled man. By way of example only, chemical groups which permit covalent attachment to surfaces may be heteroatom-containing groups, including oxygen-containing groups such as carboxyl groups, nitrogen-containing groups such as amide groups and sulphur-containing groups such as thiol groups. Covalent bonds which can exist between the compounds of the invention and the desired supports include but are not limited to ether, ester, amide, amine, sulfide, thioether and thioester bonds. Thus, for example, an ester link may have been formed from an alcohol moiety on the support and a carboxylic acid moiety within the molecule of the invention or vice versa. Alternatively, covalent attachment of the molecules of the invention to surfaces may be achieved via connections which do not involve heteroatoms, for instance via alkene-vinyl or vinyl-vinyl group connections, wherein either the alkene or vinyl group is within the molecule of the invention and the other necessary group is on a desired surface. Cycloaddition reactions may also be used to covalently attach the molecules of the invention to a desired surface.

Preferably, said covalent attachment is between the $R_2$ group of the compound and the support. Thus, preferably —$R_2$ comprises or is modified to comprise, a chemical group which permits covalent attachment to the desired support.

When the compounds of the present invention are attached to a desired solid support via a covalent bond between —$R_2$ and the support, —$R_2$ preferably comprises a carboxyl group, said carboxyl group permitting covalent attachment to the support. More preferably, in the form as it is attached to the solid support, —$R_1$—$R_2$ is selected from the group consisting of —NHCH(CH$_3$)CO—, —NH(CH$_2$)$_5$CO—, —NH(CH$_2$)$_3$CO—, —NH(CH$_2$)$_2$CO— and —NHCH$_2$CH(CH$_3$)CO—, and most preferably $R_1R_2$ is —NHCH(CH$_3$)CO— or —NH(CH$_2$)$_5$CO—

The molecules exhibit antimicrobial activity, in particular they exert a cytotoxic effect through a direct membrane-affecting mechanism and can be termed membrane acting antimicrobial agents. These molecules are lytic, destabilising or even perforating the cell membrane. This offers a distinct therapeutic advantage over agents which act on or interact with proteinaceous components of the target cells, e.g. cell surface receptors. While mutations may result in new forms of the target proteins leading to antibiotic resistance, it is much less likely that radical changes to the lipid membranes could occur to prevent the cytotoxic effect. The lytic effect causes very rapid cell death and thus has the advantage of killing bacteria before they have a chance to multiply. In addition, the molecules may have other useful properties which kill or harm the target microbes e.g. an ability to inhibit protein synthesis, thus they may have multi-target activity.

Thus in a further aspect is provided the molecules of the invention for use in destabilising and/or permeabilising microbial cell membranes. By 'destabilising' is meant a perturbation of the normal three dimensional lipid bi-layer configuration including but not limited to membrane thinning, increased membrane permeability (typically not involving channels) to water, ions or metabolites etc. which also impairs the respiratory systems of the bacteria.

When the molecules are used against a biofilm they are preferably water soluble and $R_2$ has only 2-6, preferably 2-4 non-hydrogen atoms. Antifungal applications favour molecules in which $R_2$ has 6-20, e.g. 6-15 non-hydrogen atoms, preferably 7-20, e.g. 7-15 non-hydrogen atoms.

β and γ amino acids as well as α amino acids are included within the term 'amino acids', as are N-substituted glycines which may all be considered AA units. The molecules of the invention include beta peptides and depsipeptides.

The compounds of formulae (I) to (IV) may be peptidomimetics and peptidomimetics of the peptides described and defined herein are a further aspect of the present invention. A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule is reacting with a membrane rather than the specific active site of an enzyme, some of the problems described of exactly mimicking affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995; 46, 47), retro-inverse amide (Chorev, M. and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of the present invention will typically have 3 identifiable sub-units which are approximately equivalent in size and function to amino acids (AA units). The term 'amino acid' may thus conveniently be used herein to refer to the equivalent sub-unit of a peptidomimetic compound. Moreover, peptidomimetics may have groups equivalent to the R groups of amino acids and discussion herein of suitable R groups and of N and C terminal modifying groups applies, mutatis mutandis, to peptidomimetic compounds.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

The invention provides methods of treating microbial infections by administering the various molecules described herein. Likewise methods of destabilising microbial cell membranes are provided. The amount administered should be effective to kill all or a proportion of the target microbes or to prevent or reduce their rate of reproduction or otherwise to lessen their harmful effect on the body. The clinician or patient should observe improvement in one or more of the parameters or symptoms associated with the infection. Administration may also be prophylactic.

In a further aspect is provided a method of producing a compound of the invention.

The peptides of the invention may be synthesised in any convenient way. Generally the reactive groups present (for example amino, thiol and/or carboxyl) will be protected during overall synthesis. The final step in the synthesis will thus be the deprotection of a protected derivative of the invention.

In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OP-ClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

References and techniques for synthesising peptidomimetic compounds and the other bioactive molecules of the invention are described herein and thus are well known in the art.

Formulations comprising one or more compounds of the invention in admixture with a suitable diluent, carrier or excipient constitute a further aspect of the present invention. Such formulations may be for, inter alia, pharmaceutical (including veterinary) or agricultural purposes or for use as sterilising agents for materials susceptible to microbial contamination, e.g. in the food industry. Suitable diluents, excipients and carriers are known to the skilled man.

The peptides defined herein exhibit broad antimicrobial activity and thus are also suitable as antiviral and antifungal agents, which will have pharmaceutical and agricultural applications, and as promoters of wound healing or spermicides. All of these uses constitute further aspects of the invention. As discussed above, use an antibiofilm agents is a preferred use of the compounds of the invention.

Methods of treating or preventing bacterial, viral or fungal infections or of treating tumours which comprises administration to a human or animal patient one or more of the peptides or peptidomimetics as defined herein constitute further aspects of the present invention.

The compositions according to the invention may be presented, for example, in a form suitable for oral, nasal, parenteral, intravenal, intratumoral or rectal administration.

As used herein, the term "pharmaceutical" includes veterinary applications of the invention.

The active compounds defined herein may be presented in the conventional pharmacological forms of administration, such as tablets, coated tablets, nasal sprays, solutions, emulsions, liposomes, powders, capsules or sustained release forms. The peptides are particularly suitable for topical administration, e.g. in the treatment of diabetic ulcers. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays which are a preferred method of administration may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Lotions, creams, solutions, gels and ointments etc. are preferred dosage forms. When $R_2$ is a linear aliphatic group it is preferably formulated as an ointment or other fatty formulation. When $R_2$ is a branched aliphatic moiety it is preferably formulated in an aqueous solution, gel or cream.

Dosage units containing the active molecules preferably contain 0.1-10 mg, for example 1-5 mg of the antimicrobial agent. The pharmaceutical compositions may additionally comprise further active ingredients, including other cytotoxic agents such as other antimicrobial peptides. Other active ingredients may include different types of antibiotics, cytokines e.g. IFN-γ, TNF, CSF and growth factors, immunomodulators, chemotherapeutics e.g. cisplatin or antibodies.

The bioactive molecules, when used in topical compositions, are generally present in an amount of at least 0.1%, by weight. In most cases, it is not necessary to employ the peptide in an amount greater than 1.0%, by weight.

In employing such compositions systemically (intra-muscular, intravenous, intraperitoneal), the active molecule is present in an amount to achieve a serum level of the bioactive molecule of at least about 5 µg/ml. In general, the serum level need not exceed 500 µg/ml. A preferred serum level is about 100 µg/ml. Such serum levels may be achieved by incorporating the bioactive molecule in a composition to be administered systemically at a dose of from 1 to about 10 mg/kg. In general, the molecule(s) need not be administered at a dose exceeding 100 mg/kg.

Methods of treating environmental or agricultural sites or products, as well as foodstuffs and sites of food production, or surfaces or tools e.g. in a hospital environment with one or more of the molecules of the invention to reduce the numbers of viable bacteria present or limit bacterial growth or reproduction or to reduce, disrupt, inhibit or otherwise weaken a biofilm constitute further aspects of the present invention.

The invention will now be further described with reference to the following non-limiting Examples and Figures, in which FIG. 1 are graphs showing the effect of 24 h treatment with rifampicin, linezolid, tetracycline and vancomycin on 24 h old biofilm of 6 different staphylococcal strains. For each strain, bars represent from left to right: negative control, positive control, treatment with antibiotic (vancomycin, linezold, tetracycline) concentration 5 mg/L, 50 mg/L, and 500 mg/L. For rifampicin, the concentrations were 0.01 mg/L, 0.1 mg/L and 1 mg/L. Values are means of three experiments ±SD. * means strong suppression of metabolic activity. ** means complete suppression of metabolic activity.

Figure 2:
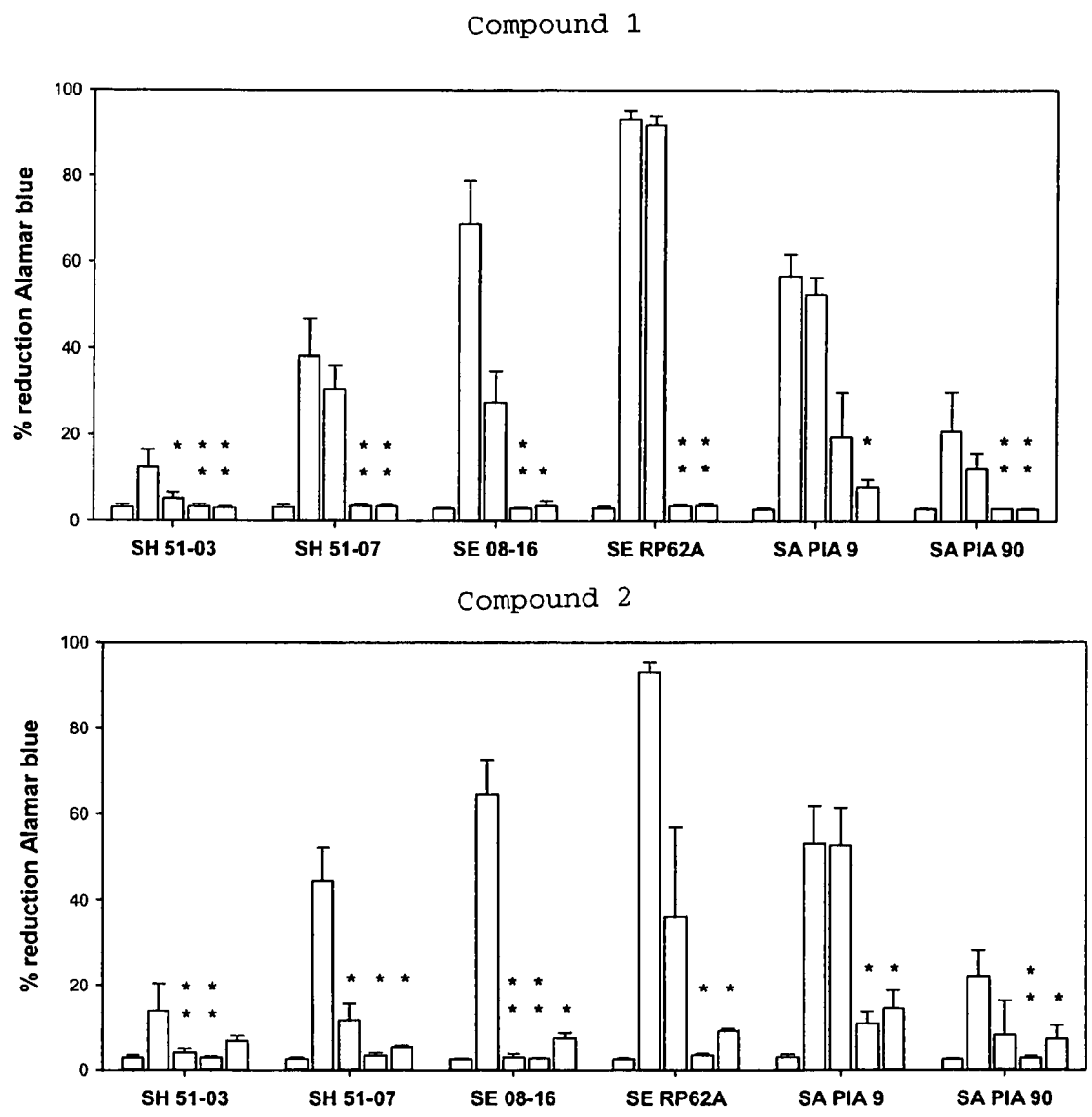

FIG. 2 are graphs showing the effect of 24 h treatment with 2 different SAMPs on 24 h old biofilm of 6 different staphylococcal strains. For each strain, bars represent from left to right negative control, positive control, treatment with SAMPs in concentration 5 mg/L, 50 mg/L, and 500 mg/L. Values are means of three experiments ±SD. * means strong suppression of metabolic activity. ** means complete suppression of metabolic activity.

Figure 3:
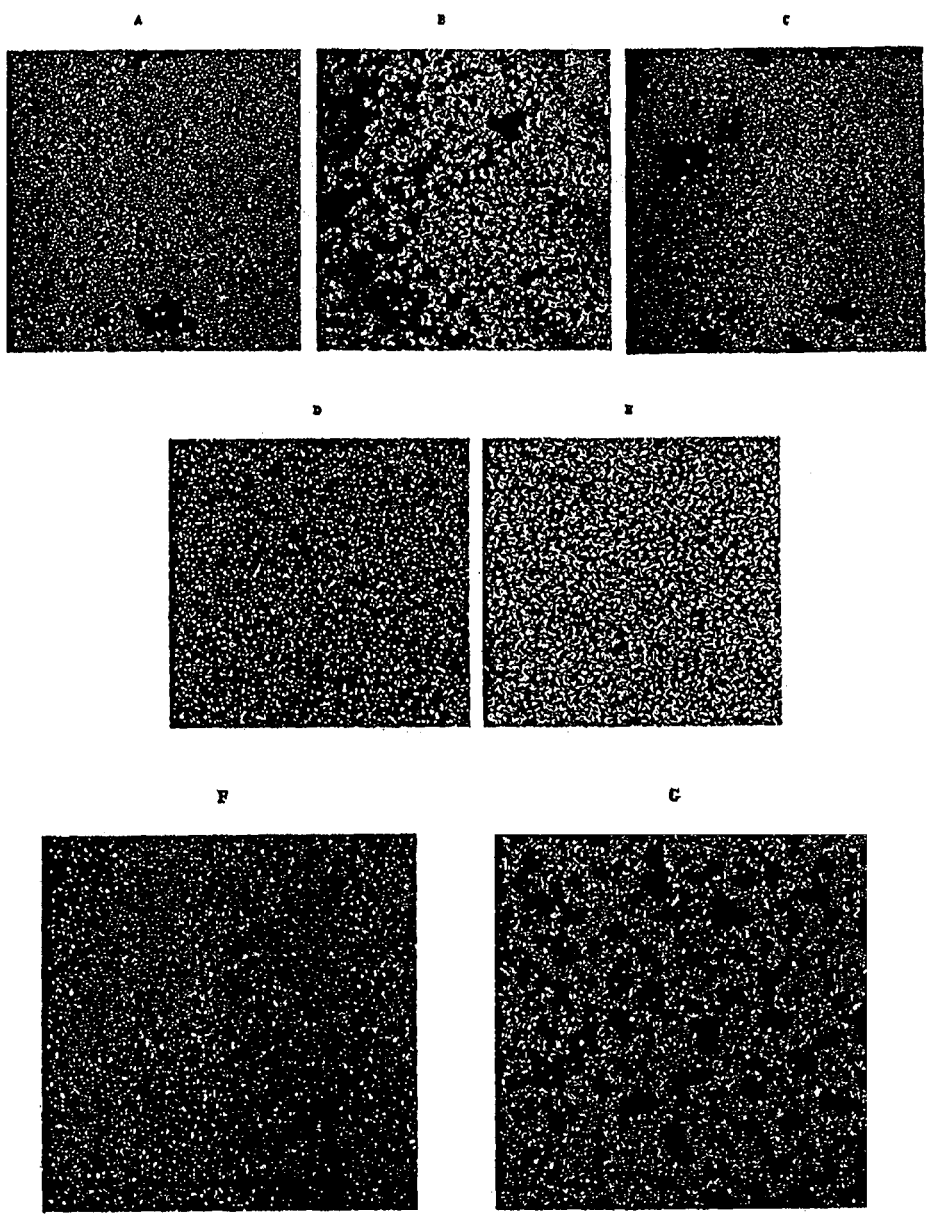

FIG. 3 are photos showing 48 h old *S. haemolyticus* 51-07 biofilm grown on cover slide discs. The biofilms were stained with LIVE/DEAD staining and investigated with confocal laser scanning microscopy. Untreated biofilm (A); biofilm treated for 24 h with vancomycin 50 mg/L (B); vancomycin 500 mg/L (C); tetracycline 50 mg/L (D); tetracycline 500 mg/L (E); Compound 1 50 mg/L (F) and Compound 1 500 mg/L (G).

Figure 4:
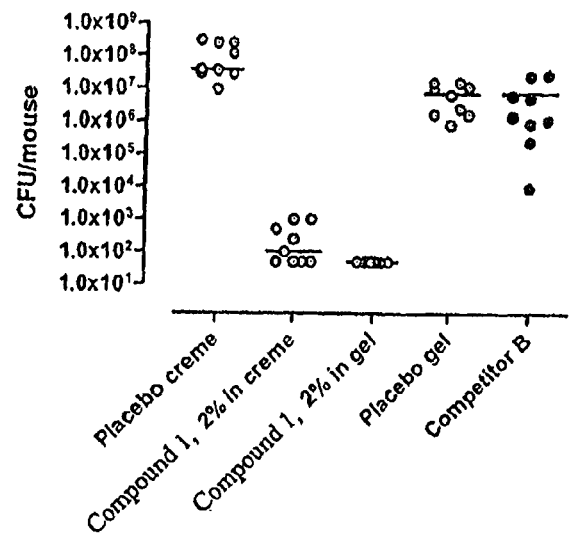

FIG. 4 is a graph showing the effect of one day topical treatment against *S. aureus* FDA486 in a murine skin infection model. Each mouse was treated at 9 am, 12 noon and 3 pm. The skin biopsy was collected at 6 pm. The median value is shown.

Figure 5:
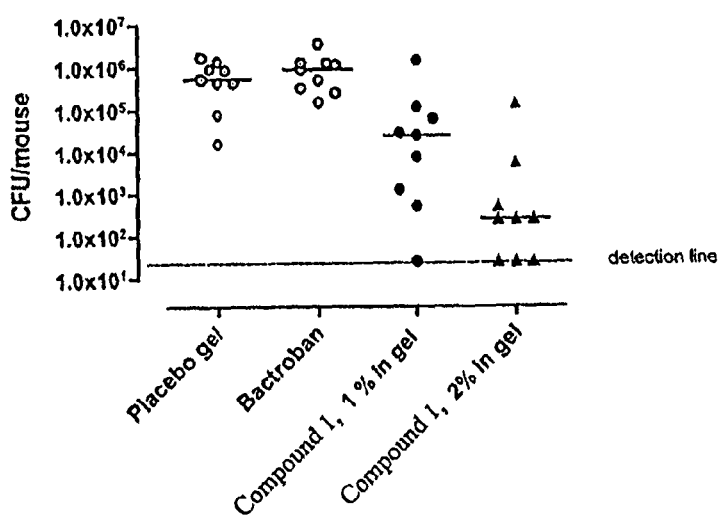

FIG. 5 is a graph showing the effect of one day topical treatment against *Streptococcus pyogenes* CS301 in a murine skin infection model. Each mouse was treated at 7 am, 10 am and 1 pm. The skin biopsy was collected at 4 pm. The median value is shown.

Figure 6:
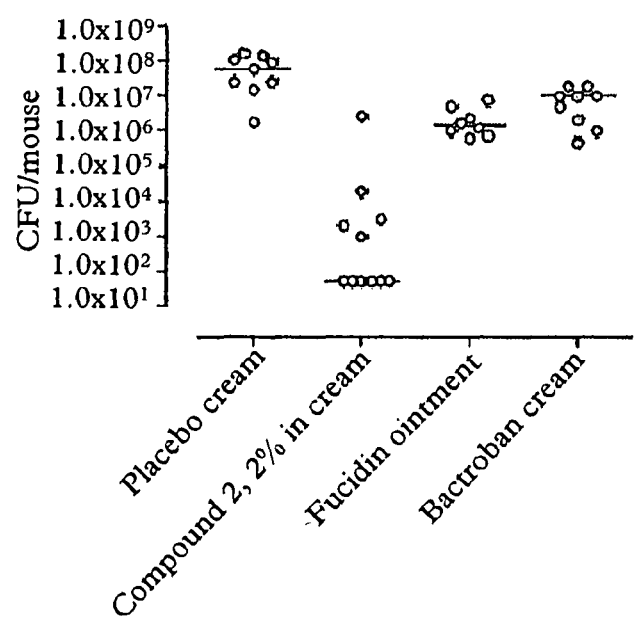

FIG. 6 is a graph showing the effect of one day topical treatment against *S. aureus* FDA486 in a murine skin infection model. Each mouse was treated at 9 am, 12 noon and 3 pm. The skin biopsy was collected at 6 pm. The median value is shown.

Figure 7:
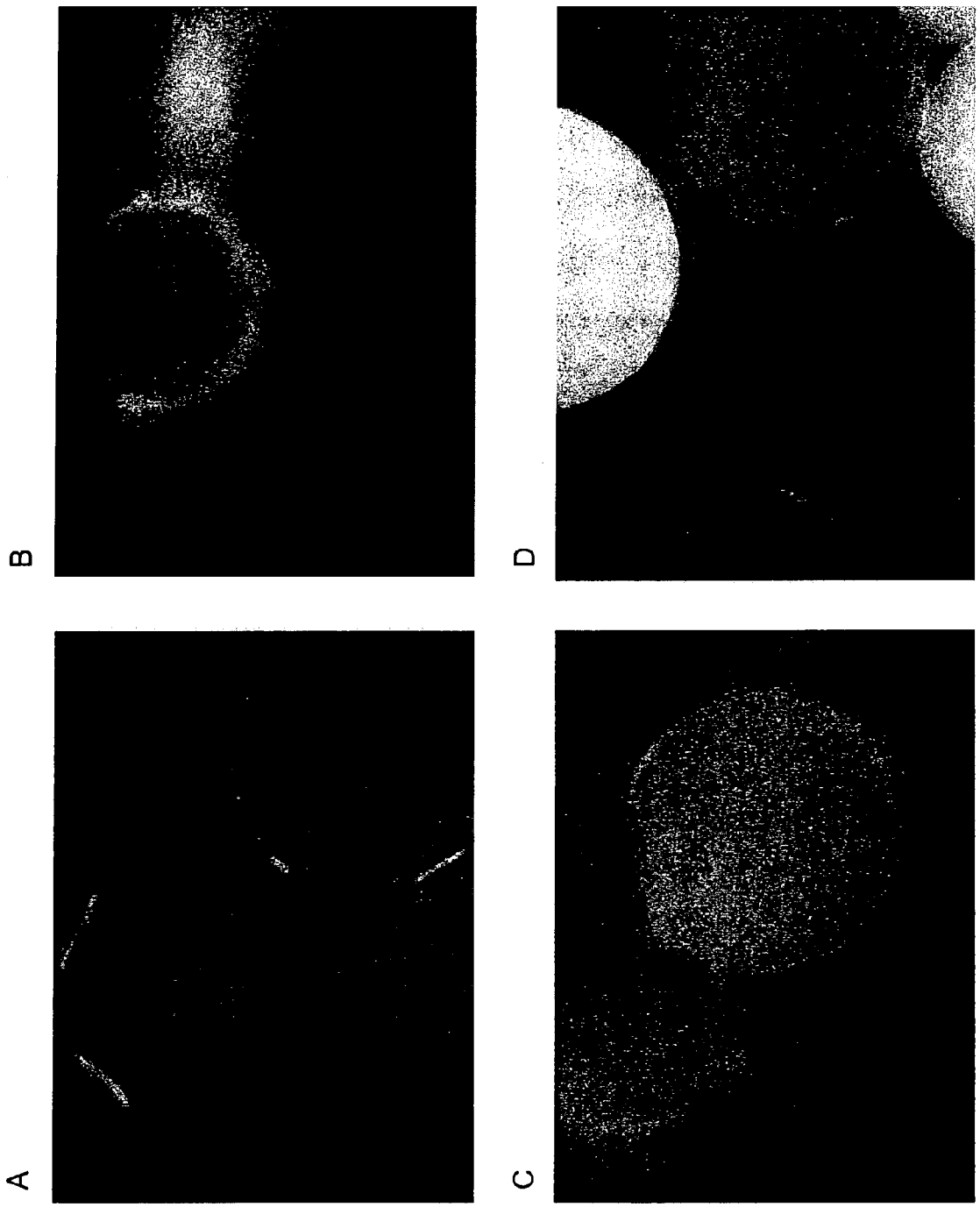

FIG. 7 is a photomicrograph of A) Uncoated aminomethylated polystyrene HL particles B) Uncoated aminomethylated polystyrene HL particles after 24 h incubation with *Staphylococcus epidermidis* C) Argininyl-(2,5,7-tri-tert-butyl)tryptophanyl-argininyl-polystyrene particles after 24 h incubation with *Staphylococcus epidermidis* D) Argininyl-(2,5,7-tri-tert-butyl)tryptophanyl-argininyl-aminohexanoyl-polystyrene particles after 24 h incubation with *Staphylococcus epidermidis*.

EXAMPLES

Example 1

Preparation and Physical, Antimicrobial and Haemolytic Properties of Molecules of the Invention Peptide Synthesis
Chemicals Protected amino acids Boc-Arg-OH, and Boc-4-phenyl-Phe were purchased from Bachem AG while Boc-4-iodophenylalanine was purchased from Aldrich. isopropylamine, propylamine, hexylamine, butylamine, hexadecylamine, isobutylamine, cyclohexylamine and cyclopentylamine making up the C-terminal of the peptide were purchased from Fluka. Diisopropylethylamine (DIPEA), 1-hydroxybenzotriazole (1-HOBt), chlorotripyrrolidinophosphonium hexafluorophosphate (PyCloP) and O-(benzotriazol-1-yl)-N,N,N',N' tetramethyluronium hexafluorophosphate (HBTU) were purchased from Fluka. 4-n-Butylphenylboronic acid, 4-t-butylphenylboronic acid, 4-biphenylboronic acid, 2-napthylboronic acid, tri ortho-tolylphosphine, benzylbromide and palladium acetate were purchased from Aldrich. Solvents were purchased from Merck, Riedel-de Haën or Aldrich.

Preparation of Amino Acids

Preparation of Boc-2,5,7-tri-tert-butyltryptophan-OH: A mixture of H2N-Trp-OH (1.8 g, 8.8 mmol), t-BuOH (4.7 g, 63.4 mmol) in trifluoroacetic acid (19 mL) is stirred at 70° C. for 3 hours. The volume of the resulting mid-brown translucent solution is reduced on a rotary evaporator at room temperature for 30 min and then triturated by means of adding 60 mL of 7% (by weight) NaHCO3 drop-wise. The gray/white granular solid obtained is then recovered by vacuum filtration and dried in vacuo at room temperature for 24 hours. The product is isolated by crystallization from a near boiling mixture of 40% ethanol in water. Volumes typically are approximately 20 mL per gram of crude product.

A first crystallization from crude produces isolated product of 80-83% purity (HPLC) with respect to all other substances in the sample and approximately 94-95% purity with respect to the known TBT analogues. Yields at this stage are in the range 60-65%.

Benzylation of Boc-4-iodophenylalanine. Boc-4-iodophenylalanine (1 equivalent) was dissolved in 90% methanol in water and neutralized by addition of caesium carbonate until a weak alkaline pH (determined by litmus paper). The solvent was removed by rotary evaporation, and remaining water in the caesium salt of Boc-4-iodophenylalanine was further reduced by repeated azeotropic distillation with toluene. The resulting dry salt was dissolved in dimethylformamide (DMF), benzylbromide (1.2 equivalents) was added and the resulting mixture was stirred for 6-8 h. At the end of the reaction DMF was removed under reduced pressure and an oil containing the title compound is formed. This oil was dissolved in ethyl acetate and the resulting solution was washed with equal volumes of citric acid solution (three times), sodium bicarbonate solution and brine. The title compound was isolated as a pale yellow oil in 85% yield by flash chromatography using dichloromethane:ethyl acetate (95:5) as eluent. Crystalline benzyl Boc-4-iodophenylalanine could be obtained by recrystallisation from n-heptane.

General procedure for Suzuki couplings: Benzyl Boc-4-iodophenylalanine (1 equivalent), arylboronic acid (1.5 equivalents), sodium carbonate (2 equivalents), palladium acetate (0.05 equivalent) and tri ortho-tolylphosphine (0.1 equivalent) was added to a degassed mixture of dimethoxyethane (6 ml/mmol benzyl Boc-4-iodophenylalanine) and water (1 ml/mmol benzyl Boc-4-iodophenylalanine). The reaction mixture was kept under argon and heated to 80° C. for 4-6 h. After cooling to room temperature the mixture is filtered through a short pad of silica gel and sodium carbonate. The filter cake was further washed with ethyl acetate. The filtrates were combined and the solvents were removed under reduced pressure. The products were isolated by flash chromatography using mixtures of ethyl acetate and n-hexane as eluent.

Preparation of Boc-Phe(4-4'-biphenyl)-OBn: The title compound was prepared in 61% yield from 4-biphenylboronic acid using the general procedure for Suzuki couplings. Boc-Phe(4-4'-biphenyl)-OBn was isolated by recrystallisation of the crude product from n-heptane.

Preparation of Boc-Phe(4-(2'-Naphtyl))-OBn: The title compound was prepared in 68% yield from 2-naphtylboronic acid using the general procedure for Suzuki couplings. Boc-Phe(4-(2'-Naphtyl))-OBn was isolated by recrystallisation of the crude product from n-heptane.

General procedure for deesterification of benzyl esters: The Benzyl ester is dissolved in DMF and hydrogenated for 2 days at ambient pressure using 10% Pd on carbon as catalyst. At the end of the reaction the catalyst is removed by filtration and the solvent is removed under reduced pressure. The free acids are isolated by recrystallisation from diethyl ether.

Preparation of Boc-Phe(4-4'-biphenyl)-OH: The title compound was prepared in 61% yield from Boc-Phe(4-4'-biphenyl)-OBn using the general procedure for deesterification.

Preparation of Boc-Phe(4-(2'-Naphtyl))-OH: The title compound was prepared in 68% yield from Boc-Phe(4-(2-Naphtyl))-OBn using the general procedure for deesterification.

General procedure for Solution phase peptide synthesis using HBTU. The peptides were prepared in solution by stepwise amino acid coupling using Boc protecting strategy according to the following general procedure. The C-terminal peptide part with a free amino group (1 eq) and the Boc protected amino acid (1.05 eq) and 1-hydroxybenzotriazole (1-HOBt) (1.8 eq) were dissolved in DMF (2-4 ml/mmol amino component) before addition of diisopropylethylamine (DIPEA) (4.8 eq). The mixture was cooled on ice and O-(benzotriazol-1-yl)-N,N,N',N' tetramethyluronium hexafluorophosphate (HBTU) (1.2 eq) was added. The reaction mixture was shaken at ambient temperature for 1-2 h. The reaction mixture was diluted by ethyl acetate and washed with citric acid, sodium bicarbonate and brine. The solvent was removed under vacuum and the Boc protecting group of the resulting peptide was deprotected in the dark using 95% TFA or acetylchloride in anhydrous methanol.

Solution phase amide formation using PyCloP. Synthesis of Boc-Arg-N(CH$_2$Ph)$_2$. A solution of Boc-Arg-OH (1 eq), NH(CH$_2$Ph)$_2$ (1.1 eq) and PyCloP (1 eq) in dry DCM (filtered through alumina) (2 ml) and DMF (1 ml). The solution was cooled on ice and DIPEA (2 eq) was added under stirring. The solution was stirred for 1 h at room temperature. The reaction mixture was evaporated, and redissolved in ethyl acetate and washed with citric acid, sodium bicarbonate and brine. The solvent was removed under vacuum and the Boc protecting group of the resulting peptide was deprotected in the dark using 95% TFA.

Peptide purification and analysis. The peptides were purified using reversed phase HPLC on a Delta-Pak (Waters) $C_{18}$ column (100 Å, 15 μm, 25×100 mm) with a mixture of water and acetonitrile (both containing 0.1% TFA) as eluent. The peptides were analyzed by RP-HPLC using an analytical Delta-Pak (Waters) $C_{18}$ column (100 Å, 5 μm, 3.9×150 mm) and positive ion electrospray mass spectrometry on a VG Quattro quadrupole mass spectrometer (VG Instruments Inc., Altringham, UK).

TABLE 1

Compounds of the invention
General compound formula: Arg-$AA_2$-Arg-$R_1R_2$

| Compound | $AA_2$ | $R_1R_2$ | Purity (HPLC) |
|---|---|---|---|
| 1 | 2,5,7-tri-tert-butyltryptophan | $NHCH(CH_3)_2$ | |
| 2 | 2,5,7-tri-tert-butyltryptophan | $NH(CH_2)_5CH_3$ | |
| 3 | 2,5,7-tri-tert-butyltryptophan | $NH(CH_2)_3CH_3$ | 87 |
| 4 | 2,5,7-tri-tert-butyltryptophan | $NH(CH_2)_2CH_3$ | 99 |
| 5 | 2,5,7-tri-tert-butyltryptophan | $NH(CH_2)_{15}CH_3$ | 80 |
| 6 | 2,5,7-tri-tert-butyltryptophan | $NHCH_2CH(CH_3)_2$ | 97 |
| 7 | 2,5,7-tri-tert-butyltryptophan | NHcyclohexyl | 95 |
| 8 | 2,5,7-tri-tert-butyltryptophan | NHcyclopentyl | 91 |
| 9 | Phe(4-4'-biphenyl) | $NHCH(CH_3)_2$ | |
| 10 | Phe(4-4'-biphenyl) | $NH(CH_2)_5CH_3$ | |
| 11 | Phe(4-(2'-Naphtyl)) | $NHCH(CH_3)_2$ | |
| 12 | Phe(4-(2'-Naphtyl)) | $NH(CH_2)_5CH_3$ | |

Antimicrobial Assay

MIC determinations on *Staphylococcus aureus*, strain ATCC 25923, Methicillin resistant *Staphylococcus aureus* (MRSA) strain ATCC 33591 and Methicillin resistant *Staphylococcus epidermidis* (MRSE) strain ATCC 27626 were performed by Toslab AS using standard methods. Amsterdam, D. (1996) Susceptibility testing of antimicrobials in liquid media, in *Antibiotics in Laboratory Medicine*. 4th ed (Lorian, V., Ed.) pp 75-78, Williams and Wilkins Co; Baltimore.

Example 2

In Vitro Broad Panel Screening of Selected Molecules of the Invention 2.0 Materials and Methods
2.1 Antimicrobials
Vials of pre-weighed Compound 1 and Compound 2 were supplied by Lytix Biopharma AS.

General compound formula: $AA_1$-$AA_2$-$AA_1$-$R_1R_2$

| | $AA_1$ | $AA_2$ | $R_1R_2$ |
|---|---|---|---|
| Compound 1 | Arg | 2,5,7-tri-tert-butyltryptophan | $NHCH(CH_3)_2$ |
| Compound 2 | Arg | 2,5,7-tri-tert-butyltryptophan | $NH(CH_2)_5CH_3$ |

2.2 Bacterial Isolates
Bacterial isolates used in this study were from various sources worldwide stored at GR Micro Ltd. and maintained, with minimal sub-culture, deep frozen at −70° C. as a dense suspension in a high protein matrix of undiluted horse serum. The species used and their characteristics are listed in Table 2. These included 54 Gram-positive bacteria, 33 Gram-negative bacteria and 10 fungi.
2.3 Determination of Minimum Inhibitory Concentration (MIC)
MICs were determined using the following microbroth dilution methods for antimicrobial susceptibility testing published by the Clinical and Laboratory Standards Institute (CLSI, formerly NCCLS):
M7-A6 Vol. 23 No. 2. January 2003 Methods for Dilution Antimicrobial Susceptibility Tests for Bacteria that Grow Aerobically; Approved Standard—Sixth Edition.
M100-S15 Vol. 25 No 1. January 2005 Performance Standards for Antimicrobial Susceptibility Testing; Fifteenth Informational Supplement.
M11-A6 Vol. 24 No. 2. Methods for Antimicrobial Susceptibility Testing of Anaerobic Bacteria; Approved Standard—Sixth Edition.
M27-A2 Vol. 22 No. 15. Reference Method for Broth Dilution Antifungal Susceptibility Testing of Yeasts; Approved Standard—Second Edition.
M38-A Vol. 22 No. 16. Reference Method for Broth Dilution Antifungal Susceptibility Testing of Filamentous Fungi; Approved Standard.

TABLE 2

Antimicrobial and toxic properties of compounds of the invention

| Compound | C. albicans (mg/L) | S. aureus (mg/L) | MRSA (mg/L) | MRSE (mg/L) | S. pyogenes (mg/L) | E. coli (mg/L) | P. aeruginosa (mg/L) | EC50 |
|---|---|---|---|---|---|---|---|---|
| 1 | 25 | <2 | <2 | <2 | <2 | 7 | 7 | 720 |
| 2 | 5 | 2 | 2 | <1 | 2 | 5 | 5 | 32 |
| 3 | 10 | 2 | 3 | <2 | 2 | | | 350 |
| 4 | 10 | 2 | 3 | <2 | 2 | | | 620 |
| 5 | >100 | 5 | 4 | 4 | 6 | >100 | >100 | 38 |
| 6 | 10 | <2 | 3 | 2 | 2 | | | 300 |
| 7 | 10 | <2 | 2 | 2 | <2 | | | 55 |
| 8 | 10 | <2 | <15 | <2 | 2 | | | 340 |

MIC estimations were performed using wet plates, containing the antibacterials or antifungals, prepared at GR Micro Ltd.

Cation-adjusted Mueller-Hinton broth (Oxoid Ltd., Basingstoke, UK and Trek Diagnostic Systems Ltd., East Grinstead, UK) (supplemented with 5% laked horse blood for *Streptococcus* spp., *Corynebacterium jeikeium* and *Listeria monocytogenes*) was used for aerobic bacteria, with an initial inoculum of approximately $10^5$ colony-forming units (CFU)/mL.

*Haemophilus* test medium (Mueller-Hinton broth containing 0.5% yeast extract and *Haemophilus* test medium supplement which contains 15 mg/L of each of haematin and NAD, all obtained from Oxoid Ltd., Basingstoke, UK) was used for the *Haemophilus influenzae* and inoculated with approximately $10^5$ CFU/mL.

Supplemented *Brucella* broth (SBB) was used for the anaerobic strains with an inoculum of approximately $10^6$ CFU/mL. SBB is a broth consisting of 1% peptone, 0.5% 'Lab-lemco', 1% glucose and 0.5% sodium chloride supplemented with 5 μg/L haemin and 1 μg/L vitamin K (both obtained from Sigma Aldrich Ltd.)

Yeast and filamentous fungal MIC were performed in MOPS buffered RPMI 1640 medium (MOPS buffer obtained from Sigma Aldrich Ltd., RPMI 1640 obtained from Invitrogen Ltd, Paisley, Scotland). The yeast inocula were in the range $7.5\times10^2$-$4\times10^3$ CFU/mL and the filamentous fungi approximately $8\times10^3$-$1\times10^5$ CFU/mL Following normal practice all the plates containing Mueller-Hinton broth were prepared in advance, frozen at −70° C. on the day of preparation and defrosted on the day of use. Fungal, *Haemophilus* and anaerobic MIC determinations were all performed in plates prepared on the same day.

3.0 Results

The results are shown in Table 3 as a single line listing.

The MIC data obtained is very encouraging and indicates that the peptides have quite a broad spectrum of activity.

TABLE 1

Single line list of the in vitro activity of two novel antimicrobial peptides against a panel of Gram-positive bacteria, Gram-negative bacteria and fungi.

| Species and properties | Compound 1 (mg/L) | Compound 2 (mg/L) |
|---|---|---|
| *Candida albicans* ATCC90028 - reference strain | 32 | 4 |
| *Candida albicans* ATCC24433 - reference strain | 64 | 8 |
| *Candida tropicalis* ATCC750 - reference strain | 4 | 4 |
| *Candida parapsilosis* ATCC90018 - reference strain | 64 | 8 |
| *Candida (Issatchenkia) krusei* ATCC6258 - reference strain | 8 | 32 |
| *Aspergillus niger* - G.R. Micro collection | 32 | 4 |
| *Trichophyton mentagrophytes* - G.R. Micro collection | 8 | 4 |
| *Trichophyton interdigitale* - G.R. Micro collection | 16 | 4 |
| *Microsporum canis* - G.R. Micro collection | 16 | 4 |
| *Cryptococcus neoformans* - G.R. Micro collection | 8 | 2 |
| *Escherichia coli* ATCC25922 - antibiotic-susceptible type strain | 32 | 4 |
| *Escherichia coli* ATCC32518 - β-lactamase positive type strain | 32 | 8 |
| *Escherichia coli* - multi-drug resistant clinical isolate | 32 | 8 |
| *Klebsiella aerogenes* NCTC11228 - antibiotic-susceptible type strain | 64 | 8 |
| *Klebsiella aerogenes* - multi-drug resistant clinical isolate | 32 | 8 |
| *Enterobacter* sp - antibiotic-susceptible clinical isolate | 64 | 8 |
| *Enterobacter* sp - multi-drug resistant clinical isolate | ≧128 | 8 |
| *Pseudomonas aeruginosa* ATCC27853 - antibiotic-susceptible type strain | 32 | 8 |
| *Pseudomonas aeruginosa* - multi-drug resistant clinical isolate | 8 | 4 |
| *Stenotrophomonas maltophilia* - antibiotic-susceptible clinical isolate | 32 | 4 |
| *Salmonella* sp - antibiotic-susceptible clinical isolate | 16 | 8 |
| *Salmonella* sp - multi-drug resistant clinical isolate | 16 | 8 |
| *Shigella* sp - antibiotic-susceptible clinical isolate | 32 | 4 |
| *Morganella morganii* - multi-drug resistant clinical isolate | 32 | 8 |
| *Haemophilus influenzae* - β-lactamase negative clinical isolate | 32 | 16 |
| *Haemophilus influenzae* - β-lactamase positive clinical isolate | 16 | 4 |
| *Haemophilus influenzae* β-lactamase negative ampicillin-resistant clinical isolate | 16 | 8 |
| *Moraxella catarrhalis* - β-lactamase positive clinical isolate | 4 | 16 |
| *Moraxella catarrhalis* - reduced fluoroquinolone susceptibility clinical isolate | 8 | 16 |
| *Acinetobacter baumanii* - antibiotic-susceptible clinical isolate | 64 | 16 |
| *Staphylococcus aureus* ATCC 29213 - antibiotic-susceptible control | 8 | 4 |
| *Staphylococcus aureus* ATCC 25923 - antibiotic-susceptible control | 8 | 4 |
| *Staphylococcus aureus* ATCC 43300 - methicillin-resistant control strain | 8 | 4 |
| *Staphylococcus aureus* - methicillin-resistant clinical isolate | 8 | 4 |
| *Staphylococcus aureus* - multi-drug-resistant clinical isolate | 16 | 4 |
| *Staphylococcus aureus* - teicoplanin-intermediate clinical isolate | 16 | 4 |
| *Staphylococcus epidermidis* antibiotic susceptible clinical isolate | 4 | 8 |
| *Staphylococcus epidermidis* methicillin-resistant clinical isolate | 4 | 2 |
| *Staphylococcus haemolyticus* - antibiotic susceptible clinical isolate | 4 | 4 |
| *Staphylococcus saprophyticus* - antibiotic susceptible clinical isolate | 2 | 0.5 |
| *Enterococcus faecalis* - ATCC 29212 antibiotic-susceptible control strain | 16 | 4 |
| *Enterococcus faecalis* vancomycin-susceptible clinical isolate | 32 | 4 |
| *Enterococcus faecalis* vancomycin-resistant (VanA) clinical isolate | 32 | 4 |
| *Enterococcus faecalis* vancomycin-resistant (VanB) clinical isolate | ≧128 | 8 |
| *Enterococcus faecalis* high-level gentamicin-resistant clinical isolate | 64 | 8 |
| *Enterococcus faecium* vancomycin-susceptible clinical isolate | 16 | 4 |
| *Enterococcus faecium* vancomycin-resistant (VanA) clinical isolate | 32 | 4 |
| *Enterococcus faecium* vancomycin-resistant (VanB) clinical isolate | 16 | 4 |
| *Enterococcus gallinarum* vancomycin-resistant (VanC) clinical isolate | 8 | 4 |
| *Streptococcus pneumoniae* - ATCC 49619 antibiotic-susceptible control strain | 32 | 16 |

TABLE 1-continued

Single line list of the in vitro activity of two novel antimicrobial peptides against a panel of Gram-positive bacteria, Gram-negative bacteria and fungi.

| Species and properties | Compound 1 (mg/L) | Compound 2 (mg/L) |
|---|---|---|
| *Streptococcus pneumoniae* - penicillin-susceptible clinical isolate | 32 | 8 |
| *Streptococcus pneumoniae* - penicillin-intermediate clinical isolate | 32 | 16 |
| *Streptococcus pneumoniae* - penicillin-resistant clinical isolate | 32 | 16 |
| *Streptococcus pneumoniae* - multi-drug resistant clinical isolate | 32 | 16 |
| *Streptococcus pyogenes* - Macrolide (MLS) resistant clinical isolate | 16 | 8 |
| *Streptococcus pyogenes* - Macrolide (M-type) resistance clinical isolate | 16 | 8 |
| *Corynebacterium jeikeium* - antibiotic-susceptible clinical isolate | 8 | 4 |
| *Corynebacterium jeikeium* - multi-drug resistant clinical isolate | 8 | 2 |
| *Listeria monocytogenes* - antibiotic-susceptible clinical isolate | 16 | 8 |
| MU50 *Staphylococcus aureus* (MRSA) - VISA type strain | 16 | 4 |
| EMRSA3 *Staphylococcus aureus* (MRSA) - SSCmec type 1 | 8 | 4 |
| EMRSA16 *Staphylococcus aureus* (MRSA) - SSCmec type 2 | 16 | 4 |
| EMRSA1 *Staphylococcus aureus* (MRSA) - SSCmec type 3 | 16 | 4 |
| EMRSA15 *Staphylococcus aureus* (MRSA) - SSCmec type 4 | 8 | 4 |
| HT2001254 *Staphylococcus aureus* (MRSA) - PVL positive | 8 | 4 |
| *Streptococcus agalactiae* - antibiotic-susceptible clinical isolate | 8 | 8 |
| *Streptococcus agalactiae* - macrolide-resistant clinical isolate | 16 | 8 |
| Group C *Streptococcus* - antibiotic-susceptible clinical isolate | 16 | 8 |
| Group C *Streptococcus* - macrolide-resistant clinical isolate | 32 | 16 |
| Group G *Streptococcus* - antibiotic-susceptible clinical isolate | 16 | 8 |
| Group G *Streptococcus* - macrolide-resistant clinical isolate | 16 | 8 |
| *Streptococcus mitis* - antibiotic-susceptible clinical isolate | 32 | 16 |
| *Streptococcus mitis* - macrolide-resistant clinical isolate | 64 | 16 |
| *Streptococcus constellatus* - antibiotic-susceptible clinical isolate | 64 | 16 |
| *Streptococcus constellatus* - macrolide-resistant clinical isolate | 32 | 16 |
| *Streptococcus oralis* - antibiotic-susceptible clinical isolate | 64 | 16 |
| *Streptococcus oralis* - macrolide-resistant clinical isolate | 64 | 16 |
| *Streptococcus bovis* - antibiotic-susceptible clinical isolate | 32 | 8 |
| *Streptococcus bovis* - macrolide-resistant clinical isolate | 8 | 2 |
| *Streptococcus sanguis* - antibiotic-susceptible clinical isolate | 32 | 16 |
| *Streptococcus sanguis* - macrolide-resistant clinical isolate | 32 | 16 |
| *Clostridium perfringens* - antibiotic-susceptible clinical isolate | ≥128 | 32 |
| *Clostridium difficile* - antibiotic-susceptible clinical isolate | 64 | 32 |
| *Propionibacterium acnes* - antibiotic-susceptible clinical isolate | | 4 |
| *Propionibacterium acnes* - antibiotic-resistant clinical isolate | | 2 |

Example 3

In Vitro Efficacy Against Biofilms

Material and Methods
Bacterial Strains and Growth Conditions
The clinical strains used in this study are listed in Table 4.

TABLE 4

Bacterial strains used in this study; susceptibility to antibiotics and SAMPs, and biofilm profile.

| Strain | Source | MIC antibiotics (mg/L) | | | | | | MIC SAMP molecules | | Biofilm | |
|---|---|---|---|---|---|---|---|---|---|---|---|
| | | RIF | VAN | TET | LZD | GEN | OXA | Compound 1 | Compound 2 | Ica[d] | optical density |
| SW[a] TUH 51-03 | Blood culture | <0.016 | 4 | 1 | 0.5 | 64 | >256 | 8 | 4 | + | 0.37 |
| SH TUH 51-07 | Blood culture | 0.016 | 2 | 0.5 | 0.5 | 64 | >256 | 8 | 4 | + | 0.77 |
| SE[b] TUH 08-16 | Blood culture | 0.016 | 2 | 2 | 2 | 256 | 16 | 4 | 2 | + | 0.63 |
| SE RP62A ATCC 35984 | Blood culture | <0.016 | 4 | 0.5 | 1 | 8 | 8 | 8 | 4 | + | 1.33 |
| SA[c] PIA 9 | Joint fluid | <0.016 | 2 | 0.5 | 2 | 1 | 1 | 8 | 4 | + | 3.20 |

TABLE 4-continued

Bacterial strains used in this study; susceptibility to antibiotics and SAMPs, and biofilm profile.

| | | MIC antibiotics (mg/L) | | | | | | MIC SAMP molecules | | | Biofilm |
| --- | --- | --- | --- | --- | --- | --- | --- | --- | --- | --- | --- |
| | | | | | | | | Compound | Compound | | optical |
| Strain | Source | RIF | VAN | TET | LZD | GEN | OXA | 1 | 2 | Ica[d] | density |
| SA PIA90 | Joint fluid | 0.016 | 2 | 0.5 | 1 | 0.5 | 1 | 8 | 2 | + | 0.40 |

[a]SH; *Staphylococcus haemolyticus*
[b]SE; *Staphylococcus epidermidis*
[c]SA; *Staphylococcus aureus*
[d]ica; PCR detection of icaD as a marker of the operon Six staphylococcal strains (2 *S. epidermidis*, 2 *S. haemolyticus* and 2 *S. aureus*) were selected based on their previously known biofilm forming capacity. Bacteria were grown overnight at 37° C. in cation adjusted Mueller-Hinton II Broth (MHIIB).

Antibiotics, SAMPs and Susceptibility Testing Under Planktonic Growth Condition

We determined the MICs of oxacillin, gentamicin, tetracycline, vancomycin and linezolid using E-test (AB Biodisk, Solna, Sweden) and MICs of rifampicin using broth microdilution assay. Breakpoints were interpreted according to EUCAST criteria. The MIC values for Compound 1 and 2 determined with broth microdilution assay.

Biofilm Formation and Quantification of Activity Against Biofilms

Biofilm formation was induced in 96-well flat bottom microtitre plates (Nunclon Surface, NUNC). First, overnight cultures were diluted 1:100 in MHIIB (*S. epidermidis* and *S. haemolyticus*) or tryptic soy broth (TSB) with 5% glucose and 5% NaCl (*S. aureus*). 200 µl of this bacterial suspension ($10^7$ cfu/ml) was added to each well and incubated for 24 h at 37° C. After 24 h the wells were carefully washed twice with phosphate-buffered saline (PBS) to remove planktonic bacteria. The washing procedure was carefully evaluated by measuring metabolic activity of the PBS with the Alamar blue method, described in detail below.

The washed biofilms were subjected to treatment with antibiotics or SAMPs at different concentrations. Stock solutions of the tetracycline (Sigma Aldrich), vancomycin (Alpharma) and linezolid (Pfizer) were diluted in MHIIB to 5 mg/L, 50 mg/L and 500 mg/L, and rifampicin (Sigma Aldrich) was diluted in MHIIB to 0.01 mg/L, 0.1 mg/L and 1 mg/L. Trifluoroacetate salts of the SAMPs were dissolved in sterile water and diluted to 5 mg/L, 50 mg/L and 500 mg/L in MHIIB. 200 µl of antibiotics or Compound 1 or 2, in different concentrations, were added to each well and incubated for 24 h at 37° C. Positive controls were untreated biofilms only added 200 µl MHIIB. Negative controls were only 200 µl MHIIB, with no bacteria added.

The metabolic activity of the biofilm was quantified with a slightly modified method previously described by Pettit et al. Antimicrob. Agents Chemother. 2005; 49: 2612-7. Briefly, after the 24 h incubation with antimicrobial agents the wells were again washed twice with PBS and then added 250 µl MHIIB with 5% Alamar blue (AB; Biosource, Camarillo, Calif., USA). AB is a redox indicator which both fluoresces and changes colour in response to chemical reduction. The extent of reduction is a reflection of bacterial cell viability. After 1 h incubation at 37° C., absorbance was recorded at 570 and 600 nm using Versamax tuneable microplate reader (Molecular Devices, Sunnyvale, Calif., USA). All assays were performed 3 times with 8 parallels. The highest and lowest value of each run was excluded from the analyses, and the remaining 18 values were averaged.

The biofilm method quantifying metabolic activity was compared to a standard semiquantitative biomass-quantification method in 96-well microtitre plates. For these experiments we grew 24 h biofilms of all 6 staphylococcal strains and analyzed metabolic activity with AB, as described above. Biomass quantification on the 24 h biofilms was performed by staining the biofilm with crystal violet (CV). After staining, ethanol:acetone (70:30) was added to each well to dissolve remaining crystal violet along the walls of the wells. The optical density (OD) was then recorded at 570 nm using a spectrophotometer.

Biofilm Imaging

One ml aliquots of MHIIB-diluted overnight culture was used to grow *S. haemolyticus* TUH 51-07 biofilm on plastic coverslides (Thermanox, cellculture treated on one side, NUNC) in 24-well dishes (Falcon 3047, Becton Dickinson, N.J., USA) for 24 h. The coverslides were then washed carefully with PBS, moved to a new plate and treated for 24 h with tetracycline 50 mg/L and 500 mg/L, vancomycin 50 mg/L and 500 mg/L, or Compound 150 mg/L and 500 mg/L. The coverslides were washed again with 9% NaCl and stained with a LIVE/DEAD kit (Invitrogen Molecular Probes, Eugene, Oreg., USA) following the manufacturer's instructions. This stain contains SYTO 9 (green fluorescent) and propidium iodide (PI; red fluorescent), both binding to DNA. When used alone, the SYTO 9 generally stains all bacteria in a population; both those with intact and those with damaged membranes. In contrast, PI penetrates only bacteria with damaged membranes, causing a reduction in the SYTO 9 stain green fluorescence when both dyes are present. We examined treated and untreated biofilms with a Leica TCS SP5 (Leica Microsystems Cms Gmbh, Mannheim, Germany) confocal laser scanning microscope (CLSM). Images were obtained using a 63×1.2 NA HCX PL APO water immersion lens. For detection of SYTO9 (green channel), we used the 488 nm line of the argon laser and a detection bandwidth of 495-515 nm. For PI detection (red channel), we used the 561 nm line and a detection bandwidth of 615-660 nm. The two fluorescent signals were collected sequentially at 400 Hz. Image analyses and export was performed in Leica LAS AF version 1.8.2.

Statistical Analysis and Evaluations

The percent reduction of AB was calculated according to the manufacturer's formula (Trek Diagnostic System). We calculated mean and standard deviations (SD) of all repeated measurements. Pearson's two-tailed correlation between the AB method and the CV method was calculated on averaged data from all 6 staphylococcal strains. Statistical analysis was performed with SPSS for Windows software version 14.0.

In FIGS. 1 and 2 we present the crude percentage values of AB reduction, including positive and negative control. We defined two levels of antimicrobial suppression of metabolic activity. A strong suppression was obtained if an agent, after adjusting for the negative control, at a certain concentration caused ≥75% reduction of AB compared to positive control. A complete suppression was obtained if an agent at a certain concentration caused a reduction of AB≤negative control value+2SD.

As expected, the untreated biofilm showed green cells with intact cell membrane FIG. 3a. In the biofilm subjected to treatment with Compound 1 in a concentration of 50 mg/L and especially 500 mg/L almost all cells are stained red, indicating dead bacteria (FIGS. 3 f and g). In biofilm subjected to treatment with 500 mg/L tetracycline a significant part of the cells are still green indicating live bacteria with intact cell membrane (FIG. 3e). Treatment of the biofilm with vancomycin (FIG. 3d) at a concentration close to the peak values obtained in clinical practice (50 mg/L) showed predominantly green cells (live organisms).

Example 4

In Vivo Activity of Compound 1 and 2

The skin of mice was infected with *Staphylococcus aureus* or *Streptococcus pyogenes* and subsequently given a total of three treatments at three hourly intervals. Three hours after the last treatment, skin biopsies were collected and the number of colony forming units (CFUs) present in the skin sample was determined.

Results are shown in FIGS. 4, 5 and 6 expressed as the number of colony forming units per mouse.

In experiment 1 (FIG. 4), compound 1 was applied to the murine skin as part of either a cream or a gel containing 2% (w/w) of compound 1. The same cream or gel without compound 1 was used as a negative control (placebo). Bactroban 2% cream was used as a positive control. It can clearly be seen that the number of CFUs was reduced when a cream or gel containing compound 1 was applied to the murine skin, compared to the negative control, indicating that compound 1 exerted an antimicrobial effect against *Staphylococcus aureus*. The efficacy of standard clinical treatment, Bactroban 2% cream, had no significant effect under the treatment regime. The nature of the carrier, cream or gel, had no significant effect.

In experiment 2 (FIG. 5), compound 1 was applied in two different concentrations, as either a 1% or a 2% gel. A placebo gel and a known antibacterial "bactroban (mupericin)" were used as controls. It can be seen that gels containing compound 1 were more effective at reducing the number of CFUs from a *Streptococcus pyogenes* CS 301 infection than the placebo gel or the bactroban. The gel containing 2% of compound 1 was more effective than the gel containing only 1% of compound 1.

In experiment 3 (FIG. 6), compound 2 was applied in a 2% cream formulation on a *Staphylococcus aureus* FDA 486 infection in the murine skin infection model. A placebo cream and two known antibacterials, "Fucidin (fucidic acid) ointment 2%" and "Bactroban (mupericin) cream 2%" were used as controls. It can be seen that a cream containing compound 2 was more effective at reducing the number of CFUs than the placebo and fucidin or bactroban.

Example 5

Peptidic Surface Modification of Polystyrene Particles

Preparation of Coated Particles 5.1

To a 20 mL peptide reactor was added 560 mg (0.5 mmole) of aminomethylated polystyrene HL particles (100-200 mesh, 0.90 mmole/g substitution) which were then washed 2×10 min with 8 mL DCM. A further 8 mL of DCM was then added and the particles permitted to swell for 1 hour before the reactor was drained prior to the first coupling.

5.2

To 8 mL of DMF was added 3 equivalents of Boc amino-acid and 683 mg (3.6 equivalents) of O-(Benzotriazol-1-yl)-N,N,N',N'-tetramethyluronium (HBTU) coupling reagent. Immediately prior to transfer of the mixture to the reactor 0.855 mL (10 equivalents) of N-Ethyldiisopropylamine (DIPEA) was added and the mixture transferred to the reaction in one portion. The reactor was then agitated moderately whilst the reaction was permitted to run overnight at room temperature.

3.

The particles were then washed 3×15 min with 8 mL DMF and 2×10 min with 8 mL DCM.

4.

At this point a small sample was removed from the reactor and subjected to the Kaiser test in order to determine whether there was any remaining uncoupled amine.

5.

If the Kaiser test gives a positive result the procedure was repeated from and including point 2 with the same amino acid. In the event that the test was negative (no uncoupled amine remaining) 8 mL of TFA/DCM (1:1) was added to the reactor to remove the Boc group from the newly coupled amino acid and the reactor agitated moderately for 1 hour.

6.

The particles were then washed 3×15 min with 8 mL DCM and 2×10 min with 8 mL DMF.

7.

The procedure was now repeated from and including point 2 to and including point 6 with the next amino acid to be coupled.

8.

When the final amino acid unit has completed stage 5 in the procedure outlined above the particles were washed 4×15 min with 8 mL DCM and dried in the reactor under nitrogen flow for 30 min before being dried under vacuum at room temperature for 24 hours. The particles were then stored in sealed vials at 4° C.

In the manner described above, the following peptide coated particles were prepared in close to quantitative yields using the appropriate amino acids:

Argininyl-(2,5,7-tri-tert-butyl)tryptophanyl-argininyl-polystyrene (control peptide)

Argininyl-(2,5,7-tri-tert-butyl)tryptophanyl-argininyl-aminohexanoyl-polystyrene (peptide according to the invention)

Reduced Bacterial Colonization of Surface Coated Particles

The particles prepared above were incubated with *Staphylococcus epidermidis* for 24 h. The amount of bacterial colonization on the bacterial surface was determined by fluorescence microscopy (excitation frequency of 485 nm, emission frequency 498 nm) after staining of the biofilm forming bacteria by Syto9 according to standard procedures.

The effect on colonization was determined by visual inspection of photomicrographs of the polystyrene particles.

FIG. 7 below shows the photomicrograph of:
A) Uncoated aminomethylated polystyrene HL particles
B) Uncoated aminomethylated polystyrene HL particles after 24 h incubation with *Staphylococcus epidermidis*
C) Argininyl-(2,5,7-tri-tert-butyl)tryptophanyl-argininyl-polystyrene particles after 24 h incubation with *Staphylococcus epidermidis*
D) Argininyl-(2,5,7-tri-tert-butyl)tryptophanyl-argininyl-aminohexanoyl-polystyrene particles after 24 h incubation with *Staphylococcus epidermidis*.

The biofilm colonization of the polystyrene particles in FIG. 7B) can readily be observed by the fluffy, furry, nature of the surface of the particles compared to the smooth surface of the polystyrene particles in FIG. 7A). FIGS. 7C) and 7D) show the effect of the two peptide coatings on the colonization by *Staphylococcus epidermidis*. In particular, coating with Argininyl-(2,5,7-tri-tert-butyl)tryptophanyl-argininyl (FIG. 7C)) is markedly less effective than coating with Argininyl-(2,5,7-tri-tert-butyl)tryptophanyl-argininyl-aminohexanoyl (FIG. d)).

Example 6

Biofilm Formation and Quantification of Activity Against Biofilms

Biofilm formation was induced in 96-well flat bottom microtitre plates (Nunclon Surface, NUNC). First, overnight cultures were diluted 1:100 in MHIIB (*S. epidermidis* and *S. haemolyticus*) or tryptic soy broth (TSB) with 5% glucose and 5% NaCl (*S. aureus*). 200 ml of this bacterial suspension (107 cfu/ml) was added to each well and incubated for 24 h at 37° C. After 24 h the wells were carefully washed twice with phosphate-buffered saline (PBS) to remove planktonic bacteria. The washing procedure was carefully evaluated by measuring metabolic activity of the PBS with the Alamar blue method, described in detail below.

The washed biofilms were subjected to treatment with the Compounds at different concentrations.

Trifluoroacetate salts of the compounds were dissolved in sterile water and diluted to 5 mg/L, 50 mg/L and 500 mg/L in MHIIB. 200 µl of the Compounds, in different concentrations, were added to each well and incubated for 24 h at 37° C. Positive controls were untreated biofilms only added 200 µl MHIIB. Negative controls were only 200 µl MHIIB, with no bacteria added.

The metabolic activity of the biofilm was quantified with a slightly modified method previously described by Pettit et al. Antimicrob. Agents Chemother. 2005; 49: 2612-7. Briefly, after the 24 h incubation with antimicrobial agents the wells were again washed twice with PBS and then added 250 ml MHIIB with 5% Alamar blue (AB; Biosource, Camarillo, Calif., USA). AB is a redox indicator which both fluoresces and changes colour in response to chemical reduction. The extent of reduction is a reflection of bacterial cell viability. After 1 h incubation at 37° C., absorbance was recorded at 570 and 600 nm using Versamax tuneable microplate reader (Molecular Devices, Sunnyvale, Calif., USA). All assays were performed 3 times with 8 parallels. The highest and lowest value of each run was excluded from the analyses, and the remaining 18 values were averaged.

Peptide Sequences

| Peptide | Sequence |
|---|---|
| ME 143 | R-Phe(4-(2'-naphthyl))-R-NH—CH(CH3)2 |

Minimum Inhibitory Concentration (MIC) on Planctonic Bacteria

| MIC | ME 143 |
|---|---|
| 8-16 *S. epidermidis* | 32 µg/ml |
| 42-77 *S. epidermidis* | 32 µg/ml |
| 51-03 *S. haemolyticus* | 16 µg/ml |
| 51-07 *S. haemolyticus* | 16 µg/ml |
| PIA 9 *S. aureus* | 64 µg/ml |
| PIA 90 *S. aureus* | 64 µg/ml |

Minimum Biofilm Inhibitory Concentration (MBIC) for ME 143 Measured as Survival Rate (%)

| MIC | 5 µg/ml | 50 µg/ml | 500 µg/ml |
|---|---|---|---|
| 8-16 *S. epidermidis* | 100 | 75 | 6 |
| 42-77 *S. epidermidis* | 100 | 80 | 12 |
| 51-03 *S. haemolyticus* | 100 | 20 | 9 |
| 51-07 *S. haemolyticus* | 100 | 12 | 8 |
| PIA 9 *S. aureus* | 100 | 100 | 14 |
| PIA 90 *S. aureus* | 100 | 80 | 7 |

The invention claimed is:

1. A method of treating a biofilm-associated infection in a subject, said method comprising the administration to the subject of a compound of formula (II)

$$AA_1\text{-}AA_2\text{-}AA_3\text{-}R_1\text{-}R_2 \quad (II)$$

wherein $AA_1$ and $AA_3$ are independently lysine, arginine, histidine or a cationic analogue of lysine, arginine or histidine, and $AA_2$ is tributyl tryptophan or a biphenylalanine derivative;

$R_1$ is a N atom, which may be substituted by a branched or unbranched $C_1$-$C_{10}$ alkyl or aryl group, which group may incorporate up to 2 heteroatoms selected from N, O and S; and $R_2$ is an aliphatic moiety having 2-20 non-hydrogen atoms, said moiety being linear, branched or cyclic.

2. A method of inhibiting biofilm formation or removing a biofilm, said method comprising contacting said biofilm with a compound of formula (II)

$$AA_1\text{-}AA_2\text{-}AA_3\text{-}R_1\text{-}R_2 \quad (II)$$

wherein $AA_1$ and $AA_3$ are independently lysine, arginine, histidine or a cationic analogue of lysine, arginine or histidine, and $AA_2$ is tributyl tryptophan or a biphenylalanine derivative;

$R_1$ is a N atom, which may be substituted by a branched or unbranched $C_1$-$C_{10}$ alkyl or aryl group, which group may incorporate up to 2 heteroatoms selected from N, O and S; and $R_2$ is an aliphatic moiety having 2-20 non-hydrogen atoms, said moiety being linear, branched or cyclic.

3. The method of claim 1 or 2 wherein $AA_1$ and $AA_3$ are arginine.

4. The method of claim 3 wherein the biphenylalanine derivative is selected from the group consisting of Phe (4-(2'-naphthyl)), Phe (4-(1'-naphthyl)), Phe (4-4'-n-butylphenyl), Phe-(4-4←biphenyl) and Phe (4-4'-t-butylphenyl).

5. The method of claim 1 or 2, wherein $R_1$ is unsubstituted.

6. The method of claim 1 or 2, wherein $R_2$ comprises 3 to 6 non-hydrogen atoms.

7. The method of claim 1 or 2, wherein the non-hydrogen atoms of $R_2$ are carbon atoms.

8. The method of claim 1 or 2, wherein $R_2$ is a linear or branched alkyl group.

9. The method of claim 1 or 2, wherein said alkyl group is selected from the group consisting of ethyl, propyl, isopropyl, butyl, isobutyl, sec-butyl, tert-butyl, pentyl and isomers thereof, and hexyl and isomers thereof.

10. The method of claim 1 or 2, wherein —$R_1$-$R_2$ together is selected from the group consisting of —NHCH $(CH_3)_2$, —NH $(CH_2)_5CH_3$, —NH $(CH_2)_3CH_3$, —NH $(CHJ_2CH_3$, —NHCH$_2$CH$(CH_3)_2$, -NHcyclohexyl and -NHcyclopentyl.

11. The method as claimed in claim 1 or 2, wherein —$R_1$-$R_2$ together is —NHCH $(CH_3)_2$ or —NH$(CH_2)_5CH_3$).

\* \* \* \* \*